US008008257B2

(12) United States Patent
De Bold et al.

(10) Patent No.: US 8,008,257 B2
(45) Date of Patent: Aug. 30, 2011

(54) ANF FUSION PROTEINS

(75) Inventors: Adolfo J. De Bold, Manotick (CA);
Mercedes L. Kuroski De Bold,
Manotick (CA); William Sheffield,
Hamilton (CA)

(73) Assignees: University of Ottawa Heart Institute,
Ottawa, Ontario (CA); **McMaster
University**, Hamilton, Ontario (CA)

( * ) Notice: Subject to any disclaimer, the term of this patent is extended or adjusted under 35 U.S.C. 154(b) by 78 days.

(21) Appl. No.: 11/551,460

(22) Filed: Oct. 20, 2006

(65) Prior Publication Data

US 2007/0162986 A1 Jul. 12, 2007

Related U.S. Application Data

(60) Provisional application No. 60/728,867, filed on Oct. 20, 2005.

(51) Int. Cl.
*C07K 14/58* (2006.01)
*C07K 1/02* (2006.01)
*A61K 39/00* (2006.01)
*C12N 5/07* (2010.01)
*C07H 21/04* (2006.01)

(52) U.S. Cl. ............... 514/12.4; 424/192.1; 424/185.1; 435/69.7; 435/328; 536/23.4; 530/350

(58) Field of Classification Search ............... None
See application file for complete search history.

(56) References Cited

U.S. PATENT DOCUMENTS 6,514,939 B1 * 2/2003 Shimkets .................. 514/12
6,686,179 B2 * 2/2004 Fleer et al. ................ 435/69.7

OTHER PUBLICATIONS

Brake, Anthony J. et al.; alpha-Factor-Directed Synthesis and Secretion of Mature Foreign Proteins in Saccharomyces cerevlsiae; Proceedings of the National Academy of Sciences (1984); 81; 4642-4646.
Brunner-La Rocca, Hans Peter at al.; Therapeutic benefits of increasing natriuretic peptide levels; Cardiovascular Research (2001); 510-520.
De Bold, Adolfo at al.; Natriuretic Peptides; Handbook of Physiology; Section 7—The Endocrine System; vol. III, Oxford University Press (2000); 377-409.
Guo, Xiaobing et al.; Prevention of remodeling in congestive hart failure due to myocardial infarction by blockade of the renin-angiotensin system; Expert Rev. Cardiovasc. Ther. 3(4); (2005); 717-732.
Kort, Jens J. at al.; Receptors for Atrial Natriuretic Peptide (ANP) and Cyclic GMP Responses in Hela Cells; Biochemical and Biophysical Research Communications; vol. 168, No. 1, (1990); 148-154.
Kuhn, Michaela; Molecular physiology of natriuretic peptide signalling; Basic Res Cordial 99; 76-82 (2004).
Kuroski De Bold, Mercedes L.; Atrial Natriuretic Factor and Brain Natriuretic Peptide Gene Expression in the Spontaneous Hypertensive Rat During Postnatal Development; American Journal of Hypertension; (1998); 11:1006-1018.
Lal, Avtar at al.; Prevention of High Salt Diet-Induced Cardiac Hypertrophy and Fibrosis by Spironolactone; American Journal of Hypertension; (2003); 16:319-323.
Marques, Janey A. et al.; A Barbourin-albumin Fusion Protein that Is Slowly Cleared In Vivo Retains the Ability to Inhibit Platelet Aggregation In Vitro; Thromb Haemost (2001); 85: 902-908.
Sarda, Inder R. et al.; Optimization of Atrial Natriuretic Factor Radioimmunoassay; Clinical Biochemistry; (1989)I vol. 22; 11-15.
Sackner-Bernstein, Jonathan D. et al.; Short-term Risk of Death After Treatment With Nesiritide for Decompensated Heart Failure; Journal of American Medical Association; (2005); vol. 293, No. 15; 1900-1905.
Sheffield, William P. et al.; Effects of genetic fusion of factor IX to albumin on in vivo clearance in mice and rabbits; British Journal of Haematology, (2004); 126, 565-573.
Sheffield, William P. et al.; Prolonged in vivo anticoagulant activity of a hirudin-albumin fusion protein secreted from Pichia pastoris; Blood Coagulation and Fibrinolysis (2001); vol. 12, No. 6; 433-443.
Stoupakis, George et al.; Natriuretic Peptides: Biochemistry, Physiology, and Therapeutic Role in Heart Failure; Heart Disease (2003); vol. 5, No. 3; 215-223.
St. John Sutton, Martin G. et al.; Left Ventricular Remodeling After Myocardial Infarction: Pathophysiology and Therapy; Journal of the American Heart Association/Circulation; (2000); 101; 2981-2988.
Tremblay, Johanne et al.; Increased Cyclic Guanosine Monophosphate Production and Overexpression of Atrial Natriuretic Peptide A-Receptor mRNA in Spontaneously Hypertensive Rats; Journal of Clinical Investigation (1993); vol. 92; 2499-2508.
Yokota, Naoto et al.; Dissociation of Cardiac Hypertrophy, Myosin Heavy Chain Isoform Expression, and Natriuretic Peptide Production in DOCA-Salt Rats; American Journal of Hypertension (1995); vol. 8; 301-310.
Sheffield WP, Mamdani A, Hortelano G, Gataiance S, Eltringham-Smith L, Begbie ME, Leyva RA, Liaw PS, and Ofosu FA; Effects of Genetic Fusion of Factor IX to Albumin on In Vivo Clearance in Mice and Rabbits; British Journal of Haematology; 2004; 126(4):565-73.
Sheffield WP, Wilson B, Eltringham-Smith LJ, Gataiance S, and Bhakta V.; Recombinant Albumins Containing Additional Peptide Sequences Smaller than Barbourin Retain the Ability of Barbourin-Albumin to Inhibit Platelet Aggregation; Thromb Haemost; 2005; 93(5):914-21.
Wang W., Qu Y., and Shi Y.; AlbuBNP, a Recombinant B-type Natriuretic Peptide and Human Serum Albumin Fusion Hormone, as a Long-term Therapy of Congestive Heart Failure; Pharm. Res.; 2004; 21(11):2105-2111.
Ruskoaho, "Atrial Natriuretic Peptide: Synthesis, Release, and Metabolism," Pharmacological Reviews, vol. 44, No. 4, 1992, pp. 479-602.
Holleman et al., "Truncated atrial natriuretic factor analogs retain full agonist activity," Can. J. Physiol. Pharmacol., vol. 69, 1991, pp. 1622-1627.
Schiller et al., "Superactive Analogs of the Atrial Natriuretic Peptide (ANF)," Biochemical and Biophysical Research Communications, vol. 143, No. 2, 1987, pp. 499-505.
Bovy et al., "Identification of Structural Requirements for Analogues of Atrial Natriuretic Peptide (ANP) to Discriminate between ANP Receptor Subtypes," J. Med. Chem., vol. 32, 1989, pp. 869-874.
Sagnella, "Atrial natriuretic peptide mimetics and vasopeptidase inhibitors," Cardiovascular Research, vol. 51, 2001, pp. 416-428.

* cited by examiner

Primary Examiner — Elly-Gerald Stoica
(74) Attorney, Agent, or Firm — Hovey Williams LLP

(57) ABSTRACT

A fusion protein comprising an arterial natriuretic factor (ANF) amino acid sequence linked to an albumin amino acid sequence by one or more peptide bonds is provided. The ANF amino acid sequence may be linked to the N-terminal, the C-terminal, or both the N-terminal and the C-terminal of the albumin amino acid sequence. Also provided is a nucleic acid molecule encoding the fusion protein and a vector comprising the nucleic acid molecule. Methods for treating or preventing cardiovascular or renal disease comprising administration of an effective amount of the fusion protein, or nucleic acid encoding the fusion protein, are also disclosed.

35 Claims, 5 Drawing Sheets

MRFPSIFTAVLFAASSALAAPVNTTTEDETAQIPAEAVIGYSDLEGDFDV
AVLPFSNSTNNGLLFINTTIASIAAKEEGVSLEKRSLRRSSCFGGRMDRI
GAQSGLGCNSFRYHKSEVAHRFKDLGEENFKALVLIAFAQYLQQCPFEDH
VKLVNEVTEFAKTCVADESAENCDKSLHTLFGDKLCTVATLRETYGEMAD
CCAKQEPERNECFLQHKDDNPNLPRLVRPEVDVMCTAFHDNEETFLKKYL
YEIARRHPYFYAPELLFFAKRYKAAFTECCQAADKAACLLPKLDELRDEG
KASSAKQRLKCASLQKFGERAFKAWAVARLSQRFPKAEFAEVSKLVTDLT
KVHTECCHGDLLECADDRADLAKYICENQDSISSKLKECCEKPLLEKSHC
IAEVENDEMPADLPSLAADFVESKDVCKNYAEAKDVFLGMFLYEYARRHP
DYSVVLLLRLAKTYKTTLEKCCAAADPHECYAKVFDEFKPLVEEPQNLIK
QNCELFEQLGEYKFQNALLVRYTKKVPQVSTPTLVEVSRNLGKVGSKCCK
HPEAKRMPCAEDYLSVVLNQLCVLHEKTPVSDRVTKCCTESLVNRRPCFS
ALEVDETYVPKEFNAETFTFHADICTLSEKERQIKKQTALVELVKHKPKA
TKEQLKAVMDDFAAFVEKCCKADDKETCFAEEGKKLVAASRAALGL*HHHH*
*HH* (SEQ ID NO:7)

FIGURE 4

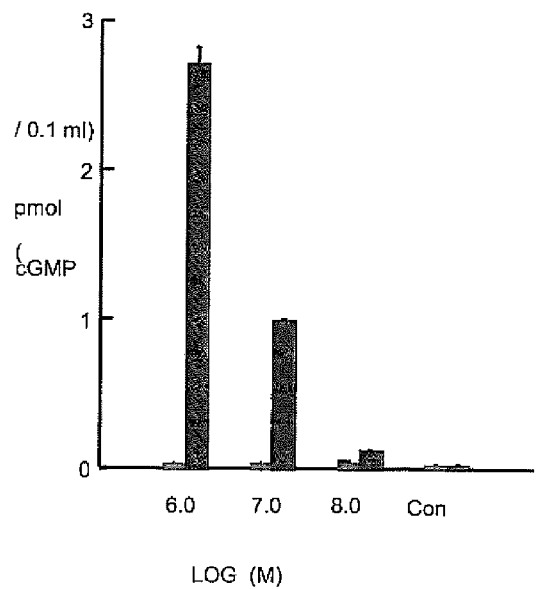
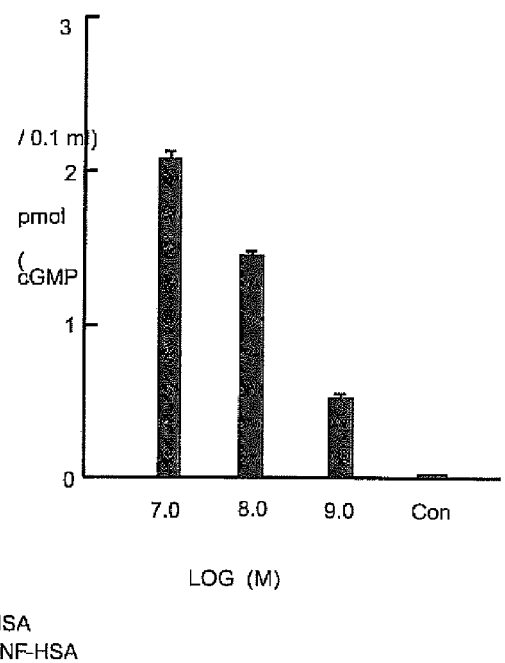
FIGURE 5

SEQUENCE LISTING

```
<160> NUMBER OF SEQ ID NOS: 7

<210> SEQ ID NO 1
<211> LENGTH: 28
<212> TYPE: PRT
<213> ORGANISM: Homo sapiens

<400> SEQUENCE: 1

Gly Pro Trp Asp Ser Ser Asp Arg Ser Ala Leu Leu Lys Ser Lys Leu
1               5                   10                  15

Arg Ala Leu Leu Thr Ala Pro Arg Ser Leu Arg Arg
            20                  25

<210> SEQ ID NO 2
<211> LENGTH: 95
<212> TYPE: DNA
<213> ORGANISM: Artificial Sequence
<220> FEATURE:
<223> OTHER INFORMATION: chemically synthesized oligonucleotide

<400> SEQUENCE: 2
tcgagaaaag aagcctgcgg agatccagct gcttcggggg caggatggac aggattggag      60
cccagagcgg actgggctgt aacagcttcc ggtac                                 95

<210> SEQ ID NO 3
<211> LENGTH: 87
<212> TYPE: DNA
<213> ORGANISM: Artificial Sequence
<220> FEATURE:
<223> OTHER INFORMATION: chemically synthesized oligonucleotide

<400> SEQUENCE: 3
cggaagctgt tacagcccag tccgctctgg gctccaatcc tgtccatcct gcccccgaag      60
cagctggatc tccgcaggct tcttttc                                          87

<210> SEQ ID NO 4
<211> LENGTH: 29
<212> TYPE: DNA
<213> ORGANISM: Artificial Sequence
<220> FEATURE:
<223> OTHER INFORMATION: chemically synthesized oligonucleotide

<400> SEQUENCE: 4
catgcggtac cacaagagtg aggttgctc                                        29

<210> SEQ ID NO 5
<211> LENGTH: 61
<212> TYPE: DNA
<213> ORGANISM: Artificial Sequence
<220> FEATURE:
<223> OTHER INFORMATION: chemically synthesized oligonucleotide
```

-continued

```
<400> SEQUENCE: 5
catggaattc ttaatggtga tggtgatggt gtaagcctaa ggcagcttga cttgcagcaa    60
c                                                                    61

<210> SEQ ID NO 6
<211> LENGTH: 39
<212> TYPE: DNA
<213> ORGANISM: Artificial Sequence
<220> FEATURE:
<223> OTHER INFORMATION: chemically synthesized oligonucleotide

<400> SEQUENCE: 6
gatcctcgag aaaagagacg cacacaagag tgaggttgc                           39

<210> SEQ ID NO 7
<211> LENGTH: 702
<212> TYPE: PRT
<213> ORGANISM: Artificial Sequence
<220> FEATURE:
<223> OTHER INFORMATION: synthesized ANF-HSA fusion protein
<220> FEATURE:
<221> NAME/KEY: MISC_FEATURE
<222> LOCATION: (1)..(85)
<223> OTHER INFORMATION: cleavable yeast alpha-factor secretory pre-
      prosequence
<220> FEATURE:
<221> NAME/KEY: MISC_FEATURE
<222> LOCATION: (86)..(113)
<223> OTHER INFORMATION: atrial natriuretic factor amino acid
      residues 99-126
<220> FEATURE:
<221> NAME/KEY: MISC_FEATURE
<222> LOCATION: (114)..(696)
<223> OTHER INFORMATION: human serum albumin amino acid residues 3-585
<220> FEATURE:
<221> NAME/KEY: MISC_FEATURE
<222> LOCATION: (697)..(702)
<223> OTHER INFORMATION: histidine tag

<400> SEQUENCE: 7

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Ser Leu Arg Arg Ser Ser Cys Phe Gly Gly Arg
                85                  90                  95

Met Asp Arg Ile Gly Ala Gln Ser Gly Leu Gly Cys Asn Ser Phe Arg
            100                 105                 110

Tyr His Lys Ser Glu Val Ala His Arg Phe Lys Asp Leu Gly Glu Glu
        115                 120                 125

Asn Phe Lys Ala Leu Val Leu Ile Ala Phe Ala Gln Tyr Leu Gln Gln
    130                 135                 140

Cys Pro Phe Glu Asp His Val Lys Leu Val Asn Glu Val Thr Glu Phe
145                 150                 155                 160

Ala Lys Thr Cys Val Ala Asp Glu Ser Ala Glu Asn Cys Asp Lys Ser
                165                 170                 175
```

```
Leu His Thr Leu Phe Gly Asp Lys Leu Cys Thr Val Ala Thr Leu Arg
            180                 185                 190

Glu Thr Tyr Gly Glu Met Ala Asp Cys Cys Ala Lys Gln Glu Pro Glu
        195                 200                 205

Arg Asn Glu Cys Phe Leu Gln His Lys Asp Asp Asn Pro Asn Leu Pro
    210                 215                 220

Arg Leu Val Arg Pro Glu Val Asp Val Met Cys Thr Ala Phe His Asp
225                 230                 235                 240

Asn Glu Glu Thr Phe Leu Lys Lys Tyr Leu Tyr Glu Ile Ala Arg Arg
                245                 250                 255

His Pro Tyr Phe Tyr Ala Pro Glu Leu Leu Phe Phe Ala Lys Arg Tyr
            260                 265                 270

Lys Ala Ala Phe Thr Glu Cys Cys Gln Ala Ala Asp Lys Ala Ala Cys
        275                 280                 285

Leu Leu Pro Lys Leu Asp Glu Leu Arg Asp Glu Gly Lys Ala Ser Ser
    290                 295                 300

Ala Lys Gln Arg Leu Lys Cys Ala Ser Leu Gln Lys Phe Gly Glu Arg
305                 310                 315                 320

Ala Phe Lys Ala Trp Ala Val Ala Arg Leu Ser Gln Arg Phe Pro Lys
                325                 330                 335

Ala Glu Phe Ala Glu Val Ser Lys Leu Val Thr Asp Leu Thr Lys Val
            340                 345                 350

His Thr Glu Cys Cys His Gly Asp Leu Leu Glu Cys Ala Asp Asp Arg
        355                 360                 365

Ala Asp Leu Ala Lys Tyr Ile Cys Glu Asn Gln Asp Ser Ile Ser Ser
    370                 375                 380

Lys Leu Lys Glu Cys Cys Glu Lys Pro Leu Leu Glu Lys Ser His Cys
385                 390                 395                 400

Ile Ala Glu Val Glu Asn Asp Glu Met Pro Ala Asp Leu Pro Ser Leu
                405                 410                 415

Ala Ala Asp Phe Val Glu Ser Lys Asp Val Cys Lys Asn Tyr Ala Glu
            420                 425                 430

Ala Lys Asp Val Phe Leu Gly Met Phe Leu Tyr Glu Tyr Ala Arg Arg
        435                 440                 445

His Pro Asp Tyr Ser Val Val Leu Leu Leu Arg Leu Ala Lys Thr Tyr
    450                 455                 460

Lys Thr Thr Leu Glu Lys Cys Cys Ala Ala Ala Asp Pro His Glu Cys
465                 470                 475                 480

Tyr Ala Lys Val Phe Asp Glu Phe Lys Pro Leu Val Glu Glu Pro Gln
                485                 490                 495

Asn Leu Ile Lys Gln Asn Cys Glu Leu Phe Glu Gln Leu Gly Glu Tyr
            500                 505                 510

Lys Phe Gln Asn Ala Leu Leu Val Arg Tyr Thr Lys Lys Val Pro Gln
        515                 520                 525

Val Ser Thr Pro Thr Leu Val Glu Val Ser Arg Asn Leu Gly Lys Val
    530                 535                 540

Gly Ser Lys Cys Cys Lys His Pro Glu Ala Lys Arg Met Pro Cys Ala
545                 550                 555                 560

Glu Asp Tyr Leu Ser Val Val Leu Asn Gln Leu Cys Val Leu His Glu
                565                 570                 575

Lys Thr Pro Val Ser Asp Arg Val Thr Lys Cys Cys Thr Glu Ser Leu
            580                 585                 590

Val Asn Arg Arg Pro Cys Phe Ser Ala Leu Glu Val Asp Glu Thr Tyr
        595                 600                 605
```

-continued

```
Val Pro Lys Glu Phe Asn Ala Glu Thr Phe Thr Phe His Ala Asp Ile
    610             615             620

Cys Thr Leu Ser Glu Lys Glu Arg Gln Ile Lys Lys Gln Thr Ala Leu
625             630             635             640

Val Glu Leu Val Lys His Lys Pro Lys Ala Thr Lys Glu Gln Leu Lys
            645             650             655

Ala Val Met Asp Asp Phe Ala Ala Phe Val Glu Lys Cys Cys Lys Ala
            660             665             670

Asp Lys Glu Thr Cys Phe Ala Glu Glu Gly Lys Lys Leu Val Ala
    675             680             685

Ala Ser Arg Ala Ala Leu Gly Leu His His His His His His
    690             695             700
```

ANF FUSION PROTEINS

RELATED APPLICATIONS

The present application claims the benefit of U.S. Provisional Application 60/728,867, filed Oct. 20, 2005, which is incorporated by reference herein.

SEQUENCE LISTING

A printed Sequence Listing accompanies this application, and has also been electronically submitted with identical contents in a computer-readable ASCII file.

FIELD OF INVENTION

The present invention relates to atrial natriuretic factor (ANF). More particularly, the present invention relates to an ANF analogue such as an ANF fusion protein.

BACKGROUND OF TH INVENTION

Acute myocardial infarction with left ventricular dysfunction and those with heart failure are major clinical entities with an extraordinary impact in our society. Administration of drugs (diuretics, angiotensin converting enzyme inhibitors, angiotensin receptor blockers, calcium channel antagonists, etc.) for treating these conditions is not without side-effects and many of the drugs are extremely expensive.

Most of the therapeutic effects of the above drugs are combined in the natriuretic peptides ANF (atrial natriuretic factor) and BNP (brain natriuretic peptide). These are polypeptide hormones produced by the heart that share potent vasodilatory, diuretic, natriuretic and antigrowth properties. They also inhibit renin and aldosterone production and sympathetic tone. In addition, these hormones exert their effects while simultaneously preventing rebound of the renin-angiotensin-aldosterone and sympathetic systems. The treatment of decompensated heart failure with ANF has been carried out with promising results. In contrast, there is some controversy regarding the therapeutic use of BNP (Sackner-Bernstein et al. Short-term risk of death after treatment with nesiritide for decompensated heart failure: a pooled analysis of randomized controlled trials. JAMA. 2005; 293:1900-1905).

The biological effects exerted by ANF and BNP are mediated, in humans, by the circulating peptides ANF[99-126] and BNP[77-108] through the membrane-bound guanylyl cyclase receptor A (NPR-A) thereby increasing intracellular 3',5-cyclic guanosine monophosphate (cGMP).[1] cGMP plasma levels and urinary excretion increase in parallel to increases in ANF and BNP plasma concentrations and hence, determination of cGMP in plasma or its excretion in urine can be used as a reflection of ANF or BNP biological activity. BNP is about 10 fold less potent than ANF in promoting cGMP production. ANF and BNP are metabolically cleared by the NPR-C receptor and by neutral endopeptidase, which is present most notably in the kidney.

ANF has anti-fibrotic properties and prevents hypertrophy of cardiocytes through a process that involves the activation of NPR-A.

Comparative binding studies to NPR-A have shown that Kd is markedly less for BNP compared to ANF (Kuhn M. Molecular physiology of natriuretic peptide signalling. Basic Res Cardiol. 2004; 99:76-82). From a therapeutic point of view therefore, the use of ANF appears more advantageous than the use of BNP. In addition, the amino acid sequence of ANF is highly conserved, which facilitates the use of non-human test systems (see Kuhn, 2004, supra.).

The peptide nature of ANF prevents its administration by ingestion and even when injected, ANF has a very short (approximately 2 min) half-life in blood due to its rapid clearance. The need for continuous intravenous (iv) infusion limits its use to a hospital setting. Coupling of ANF to human serum albumin (HSA) using a chemical maleimide linker resulted in a chemically cross-linked fusion protein that was shown to have greater stability compared to ANF alone in an in vitro human blood plasma assay (Leger R, Robitaille M, Quraishi O et al., Bioorg Med Chem Lett. 2003; 13:3571-3575). However, chemical cross-linking of ANF to serum albumins could generate errors innate to the cross-linking procedure raising important limitations concerning the exact formulation and reliability of such pharmaceutical preparations, including immunogenicity. In addition, the cost of production of ANF-HSA by chemical means is commercially prohibitive.

Therefore, there is a need for an ANF analogue with significantly longer half-life in a body fluid, for example, blood.

SUMMARY OF THE INVENTION

The present invention relates to atrial natriuretic factor (ANF). More particularly, the present invention relates to an ANF analogue such as an ANF fusion protein.

It is an object of the invention to provide an improved ANF analogue.

According to the present invention there is provided a fusion protein comprising an atrial natriuretic factor (ANF) amino acid sequence linked to an albumin amino acid sequence by one or more peptide bonds. The ANF amino acid sequence may be linked to the N-terminal, the C-terminal, or both the N-terminal and the C-terminal of the albumin amino acid sequence.

The present invention provides a nucleic acid molecule encoding a fusion protein comprising an ANF amino acid sequence linked to an albumin amino acid sequence by one or more peptide bonds.

The present invention also pertains to a vector comprising a nucleic acid sequence encoding a fusion protein comprising an ANF amino acid sequence linked to an albumin amino acid sequence by one or more peptide bonds.

The present invention provides a cell comprising a nucleic acid sequence encoding the fusion protein comprising an ANF amino acid sequence linked to an albumin amino acid sequence by one or more peptide bonds. For example, the cell may be a yeast cell.

The present invention provides a process for producing a fusion protein comprising an ANF amino acid sequence lied to an albumin amino acid sequence by one or more peptide bonds, the process comprising, expressing a nucleic acid molecule comprising a nucleic acid sequence encoding the fusion protein within a host cell. The nucleic acid molecule may further comprise a nucleotide sequence encoding a secretion signal that is operably linked to the nucleic acid sequence encoding the fusion protein, whereby the fusion protein is secreted by the host cell. The host cell may be selected from the group of bacteria, yeast, plant, and animal. The yeast cell may be *Pichia Pastoris*. The animal cell may be Chinese Hamster Ovary.

The present invention also provides a method for treating or preventing cardiovascular or renal disease comprising administration of an effective amount of the fusion protein comprising an ANF amino acid sequence linked to an albumin amino acid sequence by one or more peptide bonds. The cardiovascular or renal disease may be selected from the group consisting of conditions associated with water or electrolyte imbalance, hypertension, conditions associated with hypertension, renovascular hypertension, congestive heart failure, nephrotic syndrome, hepatic cirrhosis, pulmonary disease, renal failure due to ineffective renal perfusion or reduced glomerular filtration rate, stroke, ischemic disease, ischemia-reperfusion, cardiac remodeling and acute myocardial infarction.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 4 shows the amino acid sequence of ANF-HAS (SEQ ID NO:7). The yeast alpha-factor secretory preprosequence is underlined, the ANF99-126 sequence is indicated in bold, and the hexahistidine tag indicated in italics.

FIG. 5 shows results comparing cGMP production in HeLa cells as a function of the dose of HSA and ANF-HAS (A) versus ANF99-126 (B). Con=Control samples wherein medium was added to cells.

DETAILED DESCRIPTION

Figure 1:
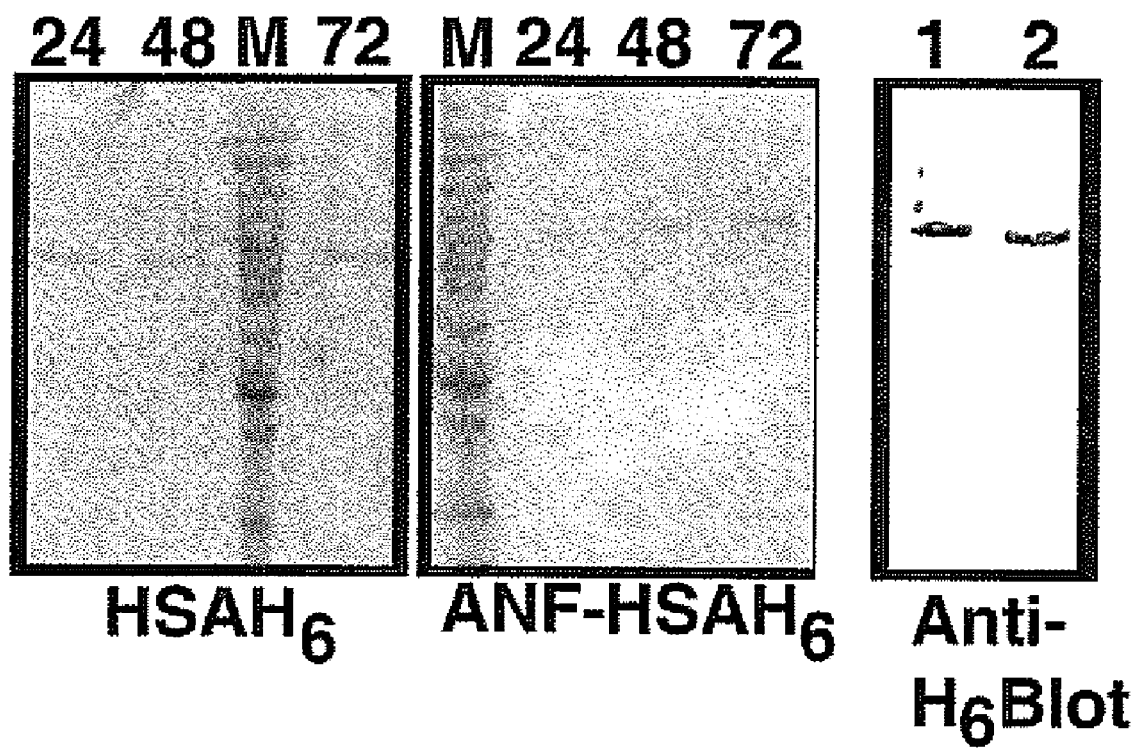
FIG. 1 shows SDS-PAGE and immunoblot analysis of conditioned media from *Pichia pastoris* clones in accordance with an embodiment of the present invention; the two panels at left are Coomassie-stained SDS gels from one clone of each kind. 72 hour samples of either putative ANF-HSAH6 (1) or HSAH6 proteins (2) were co-electrophoresed and immunoblotted with an antibody against hexahistidine (Qiagen) in the panel shown at right. Markers, M are 200, 160, 120, 100, 90, 80, 70, 60, 50, 40 and 30 kDa. Note the co-migration of the ANF-HSAH6 co-migrates with the 90 kDa marker and migrates slower than HSAH6.

The following description is of a preferred embodiment.

By "atrial natriuretic factor" or "ANF" is meant any naturally-occurring ANF amino acid sequence or any fragment, or derivative, or variant thereof that is shown to retain at least one property or activity of the naturally-occurring form, for example and without limitation, stimulation of cGMP production or decrease of mean arterial pressure in a hypertensive animal or binding to NPR-A. It is understood that, where desired, modification and changes may be made in the structure of ANF and still obtain a protein having like or otherwise desirable biological utility. Such changes may occur in natural isolates or may be synthetically introduced using site-specific mutagenesis, the procedures for which, such as mismatch polymerase chain reaction (PCR), are well known in the art. Thus, changes may be made in the sequence of the ANF amino acid sequence (or underlying nucleic acid sequence) without substantial loss of biological utility or activity and possibly with an increase in such utility or activity.

ANF from a variety of sources may be used. A non-limiting example of an ANF is human ANF (Genbank Accession No. M30262 (1990)), or human proANP (Genbank Accession No. M30262 (1990)). A nucleic acid sequence encoding ANF may be expressed in its naturally-occurring source cell type or may be expressed within a different cell type. A nucleic acid encoding ANF may be expressed in a cell type from a different species compared to the source organism of the ANF sequence. For example, a human ANF may be expressed in a yeast cell, such as *Pichia Pastoris*. ANF and nucleic acids encoding ANF from any number of species may be used, for example human, rat, dog, sheep or mouse. Human ANF is a 28-amino acid peptide (Gly Pro Trp Asp Ser Ser Asp Arg Ser Ala Leu Leu Lys Ser Lys Leu Arg Ala Leu Leu Thr Ala Pro Arg Ser Leu Arg Arg; SEQ ID NO:1) that contains a 17-residue ring formed by a disulfide bridge between two cysteine residues. As human ANF has the same pharmacological properties as rat ANF when tested in rats, the latter species is a valid test animal for human constructs. The biochemical basis for this similarity is the fact that rat and human ANF differs by only one, non-critical amino acid.

An ANF also includes a polypeptide having at least 70%, 75%, 80%, 85%, 90%, 95%, or greater identity to the polypeptide having the primary structural conformation of amino acids as shown in SEQ ID NO: 1, and exhibits the property of stimulating cGMP production, decreasing mean arterial pressure in a hypertensive animal, or binding to NPR-A.

As used herein, the term "identity", as known in the art, is the relationship between two or more polypeptide sequences (or two or more polynucleotide sequences), as determined by comparing the sequences. In the art, identity also means the degree of sequence relatedness between polypeptide (or polynucleotide) sequences, as determined by the match between strings of such sequences. Identity can be readily calculated. For example, such determinations may be made using polypeptide alignment algorithms for example, but not limited to BLAST (URL: ncbi.nlm.nih.gov/cgi-bin/BLAST/), using default parameters (Program: blastp; Expect 10; filter: default; G=11, cost to open a gap; E=1, cost to extend a gap; and W=3 word size, default is 3).

ANF sequences are well known in the art and many beneficial ANF molecules have been previously described, for example U.S. Pat. No. 6,514,939 (Shimkets et al., which is incorporated herein by reference) or U.S. Pat. No. 6,525,022 (Lowe et al. which is incorporated herein by reference). Any ANF sequence shown to have therapeutic benefit may be used in the context of the present invention.

ANF has previously been shown to provide therapeutic benefit in both humans and other animals (Stoupakis G, Klapholz M. *Heart Dis.* 2003; 5:215-223; Brunner-La Rocca H P, Kiowski W, Ramsay D et al. *Cardiovasc Res.* 2001; 51:510-520). For example, in humans, an iv injection of ANF to patients with mild hypertension or with CHF results in a decrease in systolic blood pressure, preload, afterload, renin activity and improvement in left ventricular performance without adverse side-effects. Long-term iv administration of ANF in patients with acute CHF produced a hemodynamic improvement 48 h after the start of the infusion, including a significant decrease in mean pulmonary wedge pressure, mean right atrial pressure and systemic vascular resistance. A 24 h infusion of ANF in patients with first anterior acute myocardial infarction (AMI) prevented left ventricular remodeling and improved left ventricular ejection fraction. Prevention of reperfusion injury to the myocardium by ANF infusion is suggested by a study in which patients received an intracoronary bolus of ANF within 12 h following acute myocardial infarction (AMI) and an iv infusion initiated on admission and maintained for one week ANF-treated patients showed a significant increase in left ventricular ejection fraction and regional wall motion of the infarcted segments as well as decreased left ventricular end-diastolic volume index up to six months as compared to saline-treated patients. Chronic infusion (>48 h) of ANF improves renal blood flow and glomerular filtration rate in patients with acute renal impairment associated with cardiac surgery.

The therapeutic use of ANF in normal animals and in a variety of animal models of disease supports and extends the successful use of ANF in humans. In normal animals, it has been shown that a subcutaneous (sc) injection of ANF induced a rapid and significant increase in diuresis and natriuresis.

Infusion of ANF into SHR and WKY rats resulted in a significant decrease in blood pressure and diuresis 24 h after the initiation of the infusion as well as an increase in urinary cGMP and sodium excretion and a significant decrease in blood pressure.

ANF provided protection against ischemia reperfusion injury when used in isolated rat hearts. In dogs with coronary artery occlusion, infusion of ANF started 15 min after occlusion and continuing for the next 6 hours during occlusion/reperfusion, limited myocardial necrosis, decreased left ventricular systolic pressure and left ventricular end diastolic pressure (LVEDP) as compared to baseline.

In rats, that had left anterior descending artery ligation and subsequent ventricular aneurism repair by plicating, a four-week iv infusion of ANF induced a significantly lower LVEDP, time constant of isovolumic relaxation, angiotensin converting enzyme (ACE) activity and myocardial fibrosis than those receiving saline. In a similar study, an acute iv infusion of ANF (30 min) induced marked diuresis, natriuresis, increase in urinary cGMP and a fall in BP in rats with infarction. Other studies on rats with experimentally-induced acute myocardial infarction (AMI) showed that administration of ANF to rats with experimentally-induced AMI significantly decreased systolic BP and promoted diuresis and natriuresis.

The cardiovascular actions of ANF in conscious sheep with experimental low-output cardiac failure was investigated by an iv infusion of ANF for 60 min administered on day 14 of pacing, resulting in improved cardiac output, reduced total peripheral resistance and right atrial pressure although no changes were observed in BP or plasma renin levels.

Thus ANF molecules have natriuretic, diuretic and vasorelaxant activity and may inhibit the release of aldosterone and rennin and modify heart remodeling following AMI. ANF may be used to treat or prevent cardiovascular or renal disease. In certain aspects of the present invention, an ANF analogue finds use as therapeutic agents in the treatment or prevention of various pathological conditions associated with water or electrolyte imbalance, hypertension, and tissue injury and repair. Such conditions include, for example, arterial hypertension, congestive heart failure (CHF), AMI, nephrotic syndrome and hepatic cirrhosis, pulmonary disease, and renal failure due to ineffective renal perfusion or reduced glomerular filtration rate. Further use may be found in treatment or prevention of stroke or ischemic disease.

As several clinical and experimental studies have shown that exogenous ANF administration has beneficial effects in hypertension, ischemia-reperfusion, cardiac remodeling and CHF, long term increases on circulating ANF is a possible therapeutic approach for the treatment of these pathologies. However, the peptide nature of ANF lends itself to iv administration and its relative short half-life in circulation, severely complicates the logistics of using ANF as a therapeutic agent. Therefore, the development of ANF analogues for which biological half-life is increased seems desirable.

In an aspect of the present invention an ANF analogue is a fusion protein comprising an ANF amino acid sequence linked by a peptide bond to an albumin amino acid sequence. The ANF sequence and albumin sequence can be linked by any peptide or polypeptide bond and in any fashion provided that the biological half-life of the ANF-albumin fusion protein is longer than the corresponding ANF alone. For example, the ANF and albumin sequences may be linked by a single peptide bond or may be linked by a polypeptide spacer that comprises one or more amino acid residues. As another example, ANF may be linked to either the N-terminal, the C-terminal end, or both the N-terminal and C-terminal ends of an albumin sequence. Nucleic acid sequences encoding ANF albumin fusion proteins may be prepared by any suitable standard technique. Typically, the nucleic acid will be prepared by assembling, in reading phase, the sequences encoding ANF and albumin. However, it will be understood that having ANF and albumin in the same reading phase is not required at the DNA level; for example a DNA molecule that does not comprise ANF and albumin in the same reading phase may be transcribed and spliced to produce a transcript having ANF and albumin in the same reading phase.

ANF-albumin fusions may be produced and used according to any of the standard techniques known in the art, including those disclosed in U.S. Pat. No. 6,946,134 (Rosen et al., which is incorporated herein by reference), and U.S. Pat. No. 5,876,969 (Fleer et al, which is incorporated herein by reference). Furthermore, methods of production disclosed in CN1199097 (Appl. No. 96114189.1) published Nov. 18, 1998 by Lu et al. and relating to an ANF-interleukin 2 fusion, may also be used in accordance with certain examples of the present invention.

By "albumin" or "serum albumin" is meant any naturally-occurring albumin amino acid sequence or any fragment, or derivative, or valiant thereof that is shown to retain at least one property or activity of the naturally-occurring form. Human serum albumin (HSA) is a protein of 585 amino acids in its mature form. HSA for clinical use can be produced by extraction from human blood. Albumin's stability and inert nature allows for use as a carrier of polypeptides. The use of albumin as a component of an albumin fusion protein as a carrier for various proteins has been suggested in WO 93/15199, WO93/15200, EP 413 622 and EP 399 666 (which are incorporated herein by reference) and techniques described and referred to therein may be used in the context of certain examples of the present invention.

Fusion of albumin to another protein may be achieved by standard molecular biology techniques, such that the DNA coding for HSA, or a fragment, derivative, or variant thereof is typically joined to the DNA coding for the other protein in the same reading frame. Nucleic acids encoding the fusion products are amenable for various modes of protein production and delivery, for example, without limitation, gene therapy, introduction into ex vivo cell transplants that are to reinserted into an animal, molecular farming in plants or yeasts, etc. Nucleic acids may be codon-optimized to account for codon preferences in different host cell types using methods that are well known to those of skill in the art. Vectors comprising the fused nucleotide sequences may be introduced in a suitable host by standard techniques, for example transformation, electroporation, conjugation or transfection techniques. The method of introducing foreign DNA into a host cell is not critical to the present invention. The expression may be effected in vitro from, for example, prokaryotic or eukaryotic cells in culture, or in vivo for example from a transgenic plant or animal organism.

Various expression hosts can be used to produce ANF or ANF analogues for example ANF fusion proteins. Some examples of suitable hosts cells are prokaryotic cells, animal cells, plant cells, yeasts or fungi. In prokaryotes, bacteria such as *Escherichia coli*, or *Streptomyces* may be used. In yeasts, cell types of the genus *Saccharomyces, Kluyveromyces, Pichia, Schwanniomyces*, or *Hansenula* may also be used. In animal cells, COS, CHO and C127 cells are examples of hosts that may be used. In plants, manufacture of ANF may occur in any suitable plant for example, tobacco. Of course many other suitable expression systems are known to those skilled in the art and any of these may be considered for use in production of ANF.

In preparation of a vector comprising a nucleotide sequence encoding ANF or an ANF analogue such as an ANF-albumin fusion protein standard consideration is taken with regards to components of an expression cassette, for example promoters, terminators, enhancers, leaky stop or start codons and the like. Non-limiting examples of promoters that may be used in yeast include phosphoglycerate kinase (PGK), glyceraldehyde-3-phosphate dehydrogenase (GPD), lactase (LAC4), enolases (ENO), alcohol dehydrogenases (ADH). In bacteria, examples which are not to be considered limiting in any manner of suitable promoters are promoters for the tryptophan or lactose operons. Persons skilled in the art will be aware of further expression controlling elements to achieve a desired expression pattern, for example constitutive or regulated, or over-expression or low-level expression. Furthermore, the vector may be constructed to include elements that would ease manipulation of the vector, including without limitation selectable markers, origins of replication, replication deficient vectors, or sequences for recombination into a host genome. Furthermore, the nucleic acid encoding ANF or an ANF analogue may be modified to include elements for ease of manufacture or administration of the protein product, for example, targeting sequences for directing extracellular secretion of the protein product.

An aspect of the present invention, pertains to compositions containing an effective amount of a therapeutically beneficial ANF analogue, including the nontoxic addition salts, amides and esters thereof. Compositions can be formulated physiologically tolerable liquid, gel or solid diluents, adjuvants and excipients. Dosage can readily be determined by the skilled person taking into account factors such as, age, weight, sex, condition of the patient and route of administration.

In certain examples, compositions comprising ANF analogues will typically administered parenterally by injection, either subcutaneously or intravenously. Additional formulations which are suitable for other modes of administration include suppositories, intranasal aerosols, and, in some cases, oral formulations. Compositions may be formulated in any suitable manner including, without limitation, solutions, suspensions, tablets, pills, capsules, sustained-release formulations, or powders.

The present invention will be further illustrated in the following examples.

EXAMPLES

Example 1

Biochemical and Pharmacological Characterization of ANF-HSA

1. Purification and Characterization of ANF-HSA

Constructs were prepared for expressing hexahistidine tagged human serum albumin (HSAH6) alone or in fusion with ANF.

ANF 99-126 codons were obtained by gene synthesis. Specifically, two complementary oligonucleotides:

```
ML 12004:
                                       (SEQ ID NO: 2)
5'-TCGAGAAAAGAAGCCTGCGGAGATCCAGCTGCTTCGGGGGCAGGATG
GACAGGATTGGAGCCCAGAGCGGACTGGGCTGTAACAGCTTCCGGTAC-
3'
and, ML 12005:
                                       (SEQ ID NO: 3)
5'-CGGAAGCTGTTACAGCCCAGTCCGCTCTGGGCTCCAATCCTGTCCAT
CCTGCCCCCGAAGCAGCTGGATCTCCGCAGGCTTCTTTTC-3',
``` were annealed and ligated to the 2.8 kbp KpnI-XhoI fragment of pUC19hufIX (Sheffield et al Brit J Haematol 2004; 126: 565-573) to form pUC-ANF. Several candidate clones were subjected to automated DNA sequencing, and one, with exactly the designed sequence, was selected for further work.

The HSA cDNA was then modified for combination with the ANF codons found in pUC-ANF. HSA with a 3' in-frame hexahistidine tag was amplified using the Polymerase Chain Reaction (PCR) with pC3HFUS (Sheffield et al Brit J Haematol 2004; 126:565-573) as a template using oligonucleotides:

```
ML 12006:
                                       (SEQ ID NO: 4)
5'-CATGCGGTACCACAAGAGTGAGGTTGCTC-3'
and ML 12007:
                                       (SEQ ID NO: 5)
5'-CATGGAATTCTTAATGGTGATGGTGATGGTGTAAGCCTAAGGCAGCT
TGACTTGCAGCAA C-3'.
```

The reaction product was digested with KpnI and EcoRI and inserted into the pUC-ANF construct by ligation. On transformation, sub-cloning and sequencing, a DNA plasmid of the designed sequence was obtained and designated pUC-ANF-HSA.

Figure 3:
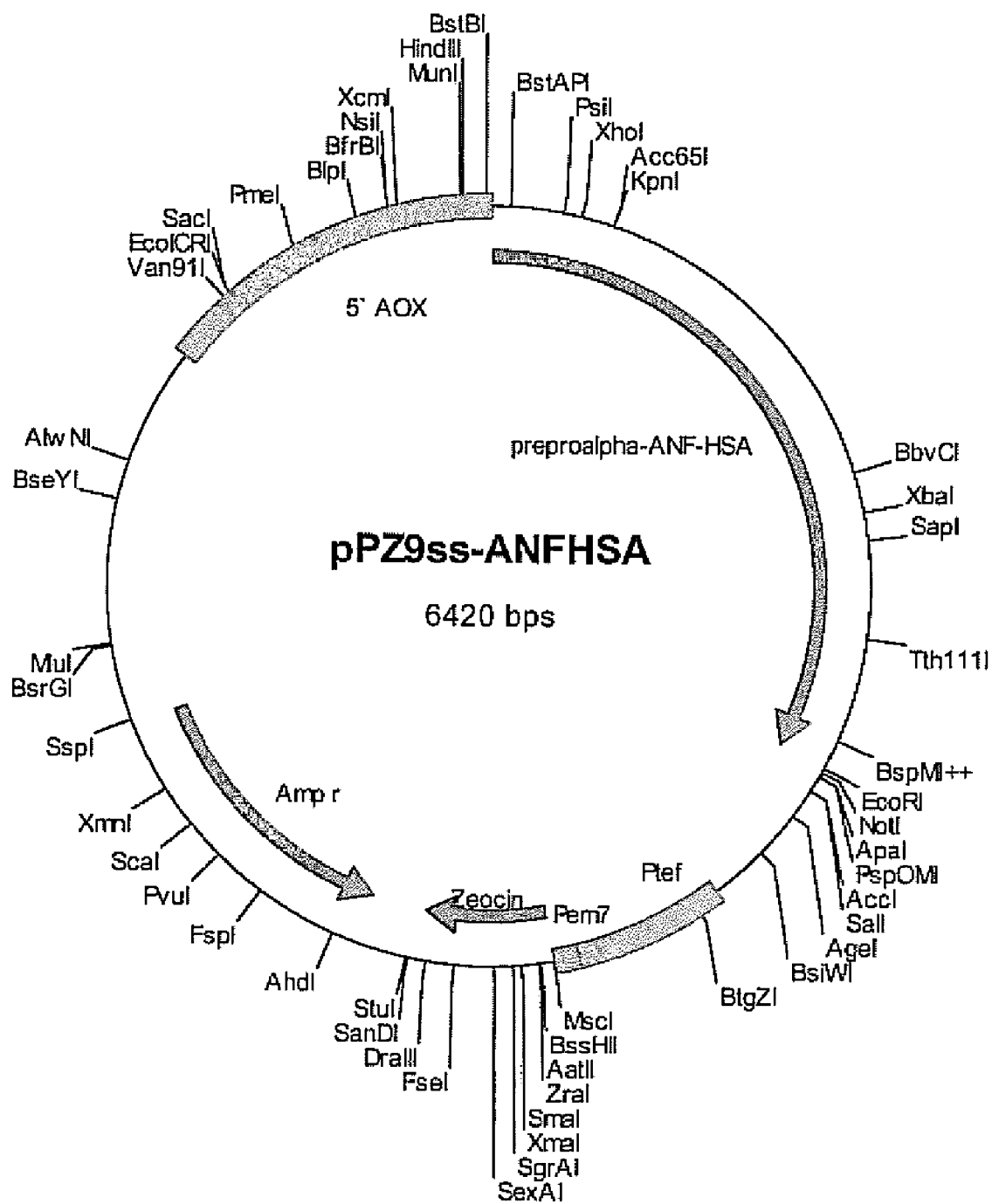
FIG. 3 shows the restriction map of pPZPss-ANF-HAS (see example 1 for details).

The fused codons for ANF and HSA were then transferred from that plasmid to pPICZ9ssamp, (Sheffield et al. Blood Coag Fibrinol 2001; 12:433-43) following XhoI and EcoRI digestion, forming pPZ9ss-ANF-HSA. Its restriction map is shown in FIG. 3.

A similar construct encoding only HSAH6 was also made, to serve as a control, in an analogous fashion, except that the primer

```
ML 12008:
                                       (SEQ ID NO: 6)
5'-GATCCTCGAGAAAAGAGACGCACACAAGAGTGAGGTTGC-3',
``` was substituted for ML 12006. This manipulation formed plasmid pPZ9ssHSAH6. After confirmation of both plasmids by DNA sequencing, they were linearized with SacI and transformed into *Pichia pastoris* strain X-33 using the Invitrogen (Carlsbad, Calif.) yeast transformation kit.

Plasmid pPZ9ss-ANF-HSA was designed to express a 702 amino acid protein, comprised (in order from N- to C-terminus) of:

an 85 amino acid cleavable yeast alpha-factor secretory pre-prosequence,
residues 99-126 of ANF,
residues 3-585 of HSA, and
six histidine residues, to facilitate purification.

The amino acid sequence of the ANF-HSA protein is shown in FIG. 4, with the cleavable yeast alpha-factor secretory pre-pro sequence underlined, the ANF 99-126 sequence bolded, and the hexahistidine tag italicized.

Similarly, the pPZ9ss-HSAH6 plasmid was designed to express a 681 amino acid protein comprised of:
an 80 amino acid cleavable yeast alpha-factor secretory pre-prosequence,
residues 1-585 of HSA, and
six histidine residues, to facilitate purification.

Three Zeocin-resistant potential clones of each construct (pPZ9ss-HSAH6 or pPZ9ss-ANF-HSA) were tested for expression in *Pichia pastoris* strain X-33. *P. pastoris* transformed with either pPZPss-HSAH6 or pPZP-ANF-HSA were induced in the presence of methanol for either 24, 48, or 72 hours prior to analysis of 0.02 ml of conditioned media by SDS-PAGE (see FIG. 1). All appeared to secrete a protein of approximately the correct size and at about the same level of expression. Importantly, these proteins become the most abundant of all those secreted by this yeast. Co-electrophoresis and immunoblotting with an anti-hexahistidine antibody suggests that the ANF-HSA protein had a slightly slower mobility than HSAH6, indicating an N-terminal extension of a few kiloDaltons, as expected and designed.

ANF-HSA is purified from media conditioned by *P. pastoris* cells permanently transformed with pPZ9-ANF-HSA and induced with methanol as per previously published protocols using nickel-chelate affinity chromatography (Marques J A, George J K, Smith I J et al. *Thromb Haemost.* 2001; 86:902-908). Briefly, the media is neutralized, precipitates removed, and the clarified media concentrated by ultrafiltration. The concentrated media is passed over Ni-NTA-agarose, and specifically bound proteins are eluted with an imidazole gradient of 10-200 mM (e.g. Sheffield W P, Smith I J, Syed S et al. *Blood Coagul Fibrinolysis.* 2001; 12:433-443). Appropriately enriched fractions are identified by SDS-polyacrylamide gel electrophoresis, pooled, concentrated to >1 mg/ml total protein concentration, aliquoted and frozen.

The purified preparation is characterized by immunoblotting and compared to unfused HSA. N-terminal amino acid sequencing and mass spectrometry (Advanced Protein Technology Centre, Hospital for Sick Children, Toronto) is used to characterize the integrity and primary structure of the purified preparation. This is appropriate because the Kex-2 processing protease cleaves after dibasic residues such as the KR dipeptide terminating the prepro-a-factor secretory sequence (Brake A J, Merryweather J P, Coit D G et al. *Proc Natl Acad Sci USA.* 1984; 81:4642-4646). It is therefore possible that cleavage could take place following the repeated Arg residues at ANF[101-102]. It is known that, as long as the portion of ANF between die disulphide-bonded—Cys105 and Cys121 is intact, ANF will retain its biological function (de Bold A J, Bruneau B G. Natriuretic Peptides. In: Fray J C S, Goodman M H, editors. Handbook of Physiology, Section 7: The Endocrine System, Volume III: Endocrine Regulation of Water and Electrolyte Balance. American Physiological Society by Oxford University Press, 2000, 2000:377-409).

2. Assessment of NPR-A-Mediated cGMP Activation Assay in HeLa Cells by ANF-HSA.

Figure 2:
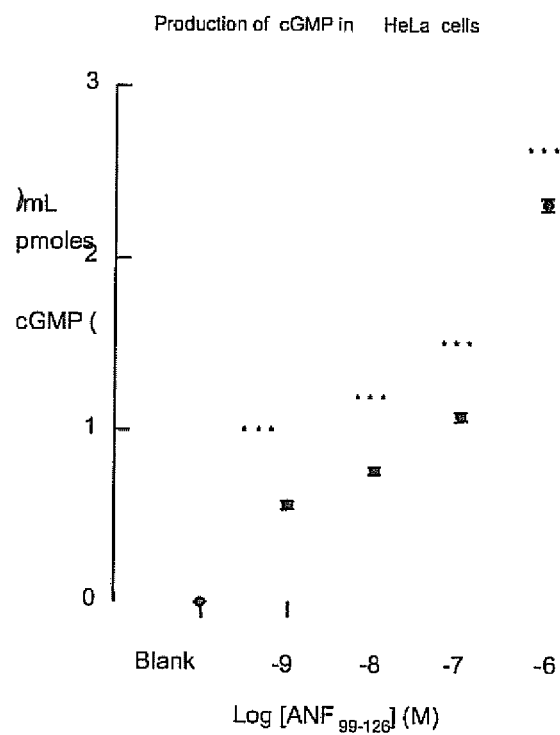
FIG. 2 shows a dose-response relationship between ANF concentration and cGMP production in accordance with a further embodiment of the present invention; HeLa cells were incubated with 10-9 to 10-6 M ANF[99-126] (n=3 plates per dose) at 37 C for 60 minutes and cGMP was measured by RNA, ***p<0.001 vs blank.

EC50 for receptor activation was compared with that of human ANF[99-126], which is the biologically active circulating form of ANF, by serially measuring cGMP accumulated in HeLa (ATCC # CCL-2) cells. These cells express the NPR-A receptor and generate cGMP upon exposure to ANF. ANF increases cGMP synthesis in these cells in a dose dependent manner with an EC50 of 5 nM (Kort J J, Koch G. *Biochem Biophys Res Commun.* 1990; 168:148-154). FIG. 2 demonstrates and confirms a dose-response relationship between synthetic ANF[99-126] concentration and cGMP production.

HeLa cells were cultured in Minimum Essential Medium (Eagle) with 2 mM L-glutamine adjusted to contain 1.5 g/L sodium bicarbonate, 0.1 mM non-essential amino acids, 1 mM sodium pyruvate and 10% heat inactivated FBS. Cells were sub-cultured when they reached 70-90% confluence. HeLa cells were harvested and resuspended in culture medium at a final concentration of $5 \times 10^4$ cells/mL. One ml of cell suspension was seeded in each well of 48-well plates and incubated overnight at 37° C. and under 5% $CO_2$ atmosphere to allow for cell adherence. Cells are washed once with fresh RPMI medium containing no FBS. Various concentrations of ANF-HSA and ANF[99-126] ranging from $10^{-6}$ M to $10^{-9}$ M were prepared in RPMI medium containing 0.5 mM IBMX and 500 µL of each dilution and added to cells. Each concentration was tested in triplicate. After one-hour incubation at 37° C., cells were washed once with PBS and lysed with 200 µL of 0.1 M HCl/well for 10 min at room temperature. The lysed cells were centrifuged at 600 g and supernatants transferred into tubes and stored at −200C pending analysis. Cyclic GMP levels were determined using a commercially available radioimmunoassay (RIA) kit. The results shown in FIG. 5 indicate that ANF-HSA fusion proteins exhibit biological activity as determined by cGMP generation in HeLa cells.

3. Pharmacokinetic Studies

To determine whether plasma levels of ANF-HSA respond in a dose-response fashion and at several time-points after a single subcutaneous (sc) or intravenous (iv) administration, native ANF is administered intravenously. cGMP levels, a biomarker for ANF activity in vivo, are determined in plasma at the specified time points and in 24 h urine. The latter determinations are used for comparison purposes with the pre-clinical studies described below. The experimental design of this study is presented in Table 1.

TABLE 1

Experimental design for pharmacokinetic study

| Group | Subgroup | Treatment | Route | Dose | Plasma sampling schedule |
|---|---|---|---|---|---|
| 1 | A (n = 5) | ANF-HSA | iv | $10^{-9}$ | Pre-dose, 0.5, 2, 6, 12, 24, 48, 72, 96, 120, 144 and 216 h |
|  | B (n = 5) |  | sc |  |  |
|  | C (n = 5) | $ANF_{99-126}$ | iv |  |  |
| 2 | A (n = 5) | ANF-HSA | iv | $10^{-8}$ |  |
|  | B (n = 5) |  | sc |  |  |
|  | C (n = 5) | $ANF_{99-126}$ | iv |  |  |
| 3 | A (n = 5) | ANF-HSA | iv | $10^{-7}$ |  |
|  | B (n = 5) |  | sc |  |  |
|  | C (n = 5) | $ANF_{99-126}$ | iv |  |  |
| 4 | (n = 5) | Vehicle | iv sc | — |  |

It should be noted that because human ANF has the same pharmacological properties as rat ANF when tested in rats, the latter species is a valid test animal for human constructs. The biochemical basis for this similarity is the fact that rat and human ANF differs by only one, non-critical amino acid.

Adult male Sprague Dawley rats are obtained with surgically implanted indwelling jugular vein and carotid artery Polyurethane 3F catheters from Charles River Laboratories. These catheters are connected to plastic vascular access ports (SoloPort Model PMINA, Instech Solomon) pre-filled with heparin (1000 U/mL) inserted in the interscapular region.

These catheters are coated with covalently bound heparin molecules thus prolonging patency for up to 30 days. These access ports allow for blood sampling in freely moving animals.

The rats are randomly assigned to six treatment groups. Rats (n=30) are administered a single injection of ANF-HSA (iv or sc) or ANF[99-126] (iv) ($10^{-9}$, $10^{-8}$ and $10^{-7}$ nmol/kg). Previous kinetic studies showed that $10^{-9}$ M of ANF[99-126] significantly enhances cGMP production in these animals while a dose of $10^{-10}$ M was without effect (Tremblay J, Huot C, Willenbrock R C et al. *J Clin Invest*. 1993; 92:2499-2508).

Blood samples are obtained at pre-dose, 0.5, 2, 6, 12, 24, 48, 72, 96, 120, 144 and 216 h after injection.

Plasma levels of endogenous ANF are determined by radioimmunoassay (RIA; Sarda I R, de Bold M L, de Bold A J. *Clin Biochem*. 1989; 22:11-15). Plasma ANF-HSA are determined by ANF/RIA after HPLC separation of endogenous ANF and ANF-HSA using standard techniques (Yokota et al. Am J Hypertens. 1995; 8:301-310). Plasma cGMP levels are determined using commercially available RIA kits.

Pharmacokinetic analysis will be conducted by the non-compartmental method (WinNonlin, Pharsight Corp. Mountain View, Calif.). The mean plasma concentration of the analyte of interest at each time point is used in the analysis. A linear up/log down trapezoidal method is used to calculate the AUC[0-t]. Extrapolation to infinity AUC[0-∞] is done by dividing the last observed concentration by the terminal elimination rate constant. Data is uniformly weighted for these analyses.

These results provide the pharmacokinetics of ANF-HSA after subcutaneous (sc) and intravenous (iv) administration. In addition, the kinetics of cGMP stimulation by ANF-HSA or ANF[99-126] after iv administration allow a comparison of effectiveness in increasing plasma cGMP levels.

Example 2

Pre-Clinical Studies Using ANF-HSA on Models of Cardiovascular Disease

1. Arterial Hypertension

Rats with established, genetically-determined arterial hypertension will experience a sustained decrease in blood pressure following a sc injection of ANF-HSA. This analysis determines the length and magnitude of blood pressure and urinary cGMP response to a single sc injection of ANF-HSA in SHR and in their control strain WKY. A summary of the experimental protocol is shown in Table 2.

Eight-week old SHR and WKY are housed in metabolic cages and a dose of ANF-HSA that induces the most significant biological effects as determined in the pharmacokinetic studies described above is used as the starting dose. This and two increments of 10 nmol/kg each will be sc injected. Control rats receive 0.9% saline sc. Mean arterial pressure (MAP) is determined by tail plesthysmography daily following injection. Plasma levels of endogenous ANF and ANF-HSA are determined as described above. Urinary cGMP levels are determined in 24-h collections to monitor for ANF-like activity. Animals are kept for 14 days after injection or until a significant effect on blood pressure is no longer detected.

These experiments allow determination of the dose of ANF-HSA required to achieve a significant lowering of MAP in a hypertensive setting as well as the duration of the effect.

2. Acute Myocardial Infarction

This experiment is directed at determining whether administration of ANF-HSA sc will attenuate late cardiac remodeling following acute myocardial infarction (AMI) as measured by hemodynamic parameters and by antifibrotic and antihypertrophic actions on the myocardium.

Remodeling of the left ventricle (LV) after acute myocardial infarction leads to heart failure and death (Guo X, Saini H K, Wang J et al. *Expert Rev Cardiovasc Ther*. 2005; 3:717-732). Remodeling after infarction involves two phases. In the early phase (within 72 h) there is expansion of the infarct zone that may lead to ventricular rupture or aneurysm formation. The late phase (after 72 h) is characterized by remodeling of the whole LV and is coupled with time-dependent dilatation, mural hypertrophy and cardiac fibrosis (Sutton M G, Sharpe N. *Circulation*. 2000; 101:2981-2988).

In this experiment, modifications in hemodynamics, neurohumoral profile and cardiac gene expression respectively, are determined after sc administration of ANF-HSA to rats following AMI induced by ligation of the left anterior descending coronary artery (LAD). A summary of the experimental protocol is shown in Table 3.

TABLE 2

Effects of ANF-HSA on arterial hypertension

| Group | Strain and dosage | Treatment | Dose | Route | MAP & urine sampling |
|---|---|---|---|---|---|
| 1 | SHR (n = 5) Dose 1 | ANF-HSA | Three doses are tested. Dosage and dosage schedule are determined by the pharmacokinetic studies | sc | Every 24 h for 14 days |
| 2 | WKY (n = 5) dose 1 | | | | |
| 3 | SHR (n = 5) Dose 2 | | | | |
| 4 | WKY (n = 5) Dose 2 | | | | |
| 5 | SHR (n = 5) Dose 3 | | | | |
| 6 | WHY (n = 5) Dose 3 | | | | |
| 7 | SHR control (n = 5) | Vehicle | 0 | | |
| 8 | WKY control (n = 5) | | | | |

TABLE 3

Effect of ANF-HSA on cardiac remodeling following acute myocardial infarction

| Group | Treatment | Dose | Route | Killing schedule (days) | MAP, ECO, urine and blood sampling |
|---|---|---|---|---|---|
| AMI, dose 1 days (n = 20) | ANF-HAS | Three doses are tested. Dosage and dosage schedule are determined by the pharmacokinetic studies | sc | 14 | Weekly |
| AMI, dose 2 (n = 20) | | | | | |
| AMI, dose 3 (n = 15) | | | | | |
| AMI control (n = 20) | Vehicle | 0 | | | |
| AMI Sham (n = 15) | | | | | |

Adult male SD rats (220-250 g) with LAD ligation are ordered from Charles River Laboratories to arrive in our laboratory within a week after LAD ligation or sham operation. This technique induces extensive infarcts (>30%), and the timing is chosen because it is known that most phenotypic changes occur at this time (e.g. Sutton M G, Sharpe N. *Circulation.* 2000; 101:2981-2988). The carotid artery is cannulated at source with a Polyurethane 3F catheters. Seven days after ligation or sham operation the rats are randomly subdivided into 3 sub-groups and treated as follows: 1) ANF-HSA (n=60); 2) vehicle, 0.9% saline (n=20), 3) sham-operated, vehicle, 0.9% saline (n=15). The dosage of ANF-HSA is determined from the pharmacokinetic study. The animals are killed by decapitation at 14 days after injection.

A) Hemodynamic and LV Volume Measurements.

Echocardiography is performed in all groups prior the administration of the compound (baseline), and then weekly until prior to sacrifice to allow for serial in situ determination of LV chamber size, wall thickness and mass. Briefly, immediately before echocardiograms animals are anesthetized with isofluorane. The animal's chest is shaved and then animals are placed into a left decubitus position. A 12 Mhz phase-array transducer is placed on the left hemithorax and targeted M-mode recordings are made by directing the beam toward the mid papillary level. Electrocardiographic electrodes are attached to the animal's paws and a single lead electrocardiogram is recorded on the imaging system. Briefly, a two-dimensional short axis view of the LV and M-mode tracing is recorded through the anterior and posterior LV walls at the papillary muscle level to measure the LV end-diastolic dimension (LVEDD), LV end-systolic dimension (LVESD) and interventricular septal (IVS) and posterior wall (PW) thickness is measured by the leading edge method. The sonographer measures these parameters during systole and diastole. Using pulse-wave Doppler echocardiography, signals from the ventricular inflow and outflow tracks are measured. This allows for the measurement of diastolic filling patterns (E wave/A wave ratios from mitral flow curve), velocity of flow into the right ventricle and left atrium. Left ventricular ejection fraction (LVEF) is calculated by the cube method as follows:

$$LVEF=[(LVEDD)^3-(LVESD)^3]/(LVEDD)^3$$

Stroke volume (SV) is determined by Doppler velocity recordings performed at the base of the ascending aorta. The value of SV is multiplied by heart rate (HR) to calculate cardiac output (CO). CO divided by BW is used to calculate cardiac output index (COI). Blood pressure (BP) is measured by tail plethysmography. BP, HT and body weight (BW) is recorded weekly.

B) Tissue Sample Collection.

Hearts from one half of the animals (n=5) from each sub-group are used for the estimation of infarct size and collagen deposition. The atria are trimmed from the ventricles. The right ventricle (RV) and the LV, including septum are separated, weighed, formalin fixed and paraffin embedded. Infarct size is quantified histologically by planimetry. The LV is cut into three transverse sections; apex, middle ring (~3 mm) and base. From the middle ring, 5-μm sections are cut at 100-μm intervals. Two sections are stained, one with Sirius red F3BA and the other section with hematoxilin-eosin. Each fields of the non-infarcted myocardium are digitized and then the area of interstitial fibrosis calculated as the ratio of the sum of the total area of interstitial fibrosis to the sum of the total area of connective tissue area and the cardiocyte area in all the LV fields of the section using Inage Pro Plus imaging software (media Cybernetics, Silver Spring, Md.). Perivascular areas are not included in this analysis. Average myocyte cross-sectional area is calculated (Lal A, Veinot J P, Leenen F H. *Am J Hypertens.* 2003; 16:319-323).

C) Neurohumoral Profiling.

Plasma cGMP, plasma renin activity and aldosterone levels will be determined using commercially available radioimmunoassay (RIA) kits. Plasma levels of endogenous ANF will be determined by RIA (Sarda I R, de Bold M L, de Bold A J. *Clin Biochem.* 1989; 22:11-15). Plasma ANF-HSA will be determined by ANF/RIA after HPLC separation of endogenous ANF and ANF-HSA.

D) Evaluation of Cardiac Gene Expression

Hearts from the other half of the animals (n=5) from each sub-group are excised and dissected into right atrium (RA), left atrium (LA), right ventricle (RV), and left ventricle (LV). LV is divided into: a) viable left ventricle and b) infarct scar. Total RNA is isolated from each chamber and from the LV (non-infarcted) using TriZol reagent.

Atrial natriuretic factor (ANF), brain natriuretic factor (BNP), collagen type I and III, $\alpha$ and $\beta$ myosin heavy chain, and sarcoplasmic-reticulum calcium adenosine triphosphatase (SERCA2 ATPase) are subjected to Northern Blot analysis (Kuroski, de Bold M L. *Hypertension.* 1998; 11:1006-1018).

Given the inhibitory effects of ANF on cardiac fibrosis and hypertrophy in vitro and in vivo, ANF-HSA modifies, or prevents the progression of cardiac late remodeling after acute myocardial infarction. A similar effect on the neurohumoral activation observed following acute myocardial infarction (AMI) is also expected.

A product resulting from the genetic fusion of ANF to HSA is expected to have longer half-life than ANF while preserving the biological actions of ANF thus providing for a compound with pharmacokinetic advantage over native ANF.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A fusion protein comprising an atrial natriuretic factor (ANF) amino acid sequence comprising amino acid residues 86 to 113 of SEQ ID NO: 7 linked to an albumin amino acid sequence by one or more peptide bonds, wherein said fusion consists of amino acid residues of SEQ ID NO: 7 and the protein has a longer biological half-life than the corresponding ANF, and retains at least one pharmacological property of the naturally occurring ANF.

2. A nucleic acid molecule encoding the fusion protein of claim 1.

3. A vector comprising a nucleic acid sequence encoding the fusion protein of claim 1.

4. The vector of claim 3, wherein the vector is pPIC-ANF-HSAH6.

5. A cell comprising a vector as in claim 3.

6. The cell according to claim 5, wherein the cell-type is a yeast cell.

7. A process for producing the fusion protein of claim 1 comprising:
   a) introducing a vector comprising the nucleic acid sequence encoding the fusion protein of claim 1 into a host cell;
   b) expressing the fusion protein; and
   c) optionally purifying the fusion protein by Ni-NTA agarose chromatography.

8. The process of claim 7, wherein the vector comprises a nucleic acid encoding a secretion signal that is operably linked to the nucleic acid sequence encoding the fusion protein, whereby the fusion protein is secreted by the host cell.

9. The process of claim 7, wherein the host cell type is selected from the group consisting of bacterial, yeast, plant, and animal cells.

10. The process of claim 9, wherein the yeast cell type is *Pichia Pastoris*.

11. The process of claim 9, wherein the animal cell type is Chinese Hamster Ovary.

12. A fusion protein produced by the process of claim 7.

13. A fusion protein comprising an atrial natriuretic factor (ANF) amino acid sequence linked to an albumin amino acid sequence by one or more peptide bonds, wherein said fusion protein comprises amino acid residues 1 to 696 of SEQ ID NO: 7 and the protein has a longer biological half-life than the corresponding ANF, and retains at least one pharmacological property of the naturally occurring ANF.

14. The fusion protein of claim 13, wherein said fusion protein comprises the amino acid sequence of SEQ ID NO: 7.

15. A nucleic acid molecule encoding the fusion protein of claim 13.

16. A vector comprising a nucleic acid sequence encoding the fusion protein of claim 13.

17. A cell comprising a vector as in claim 16.

18. The cell according to claim 17, wherein the cell-type is a yeast cell.

19. A process for producing the fusion protein of claim 13 comprising:
   a) introducing a vector comprising the nucleic acid sequence encoding the fusion protein of claim 13 into a host cell;
   b) expressing the fusion protein; and
   c) optionally purifying the fusion protein by Ni-NTA agarose chromatography.

20. The process of claim 19, wherein the vector comprises a nucleic acid encoding a secretion signal that is operably linked to the nucleic acid sequence encoding the fusion protein, whereby the fusion protein is secreted by the host cell.

21. The process of claim 19, wherein the host cell type is selected from the group consisting of bacterial, yeast, plant, and animal cells.

22. The process of claim 21, wherein the yeast cell type *Pichia Pastoris*.

23. The process of claim 21, wherein the animal cell type is Chinese Hamster Ovary.

24. A fusion protein comprising an atrial natriuretic factor (ANF) amino acid sequence linked to an albumin amino acid sequence by one or more peptide bonds, wherein said fusion protein consists of amino acid residues 1 to 113 of SEQ ID NO: 7 linked to the sequence of human serum albumin (HSA) and the protein has a longer biological half-life than the corresponding ANF, and retains at least one pharmacological property of the naturally occurring ANF.

25. The fusion protein of claim 24, wherein the ANF amino acid sequence is directly linked to the N-terminus of the albumin amino acid sequence through a peptide bond.

26. The fusion protein of claim 24, wherein the ANF amino acid sequence is linked to the N-terminus of the albumin amino acid sequence by a peptide spacer that comprises at least one amino acid residue.

27. A nucleic acid molecule encoding the fusion protein of claim 24.

28. A vector comprising a nucleic acid sequence encoding the fusion protein of claim 24.

29. A cell comprising a vector as in claim 28.

30. The cell according to claim 29, wherein the cell-type is a yeast cell.

31. A process for producing the fusion protein of claim 24 comprising:

a) introducing a vector comprising the nucleic acid sequence encoding the fusion protein of claim 24 into a host cell;
b) expressing the fusion protein; and
c) optionally purifying the fusion protein by Ni-NTA agarose chromatography.

32. The process of claim 31, wherein the vector comprises a nucleic acid encoding a secretion signal that is operably linked to the nucleic acid sequence encoding the fusion protein, whereby the fusion protein is secreted by the host cell.

33. The process of claim 32, wherein the host cell type is selected from the group consisting of bacterial, yeast, plant, and animal cells.

34. The process of claim 33, wherein the yeast cell type is *Pichia Pastoris*.

35. The process of claim 33, wherein the animal cell type is Chinese Hamster Ovary.

* * * * *